United States Patent
Glockler et al.

(10) Patent No.: US 6,488,676 B1
(45) Date of Patent: Dec. 3, 2002

(54) TWO-PIVOT SCANNING FOR LASER EYE SURGERY

(75) Inventors: Herrmann Glockler, Cupertino; Henry Price; Jeff Sobiech, both of San Jose, all of CA (US)

(73) Assignee: VISX, Incorporated, Santa Clara, CA (US)

(*) Notice: Subject to any disclaimer, the term of this patent is extended or adjusted under 35 U.S.C. 154(b) by 0 days.

(21) Appl. No.: 09/405,457

(22) Filed: Sep. 24, 1999

(51) Int. Cl.[7] ................................................ A61B 18/18
(52) U.S. Cl. ............................... 606/4; 606/5; 606/10; 606/13; 606/17; 606/18; 606/19; 356/138
(58) Field of Search ..................... 606/2, 4–6, 10–13, 606/17–19; 356/138, 139; 351/212, 246, 247

(56) References Cited

U.S. PATENT DOCUMENTS

| | | | |
|---|---|---|---|
| 4,665,913 A | 5/1987 | L'Esperance, Jr. | |
| 4,669,466 A | 6/1987 | L'Esperance | |
| 4,887,019 A | 12/1989 | Reis et al. | |
| 5,360,424 A | * 11/1994 | Klopotek | 606/4 |
| 5,391,165 A | * 2/1995 | Fountain et al. | 606/4 |
| 5,505,723 A | 4/1996 | Muller | |
| 5,520,679 A | 5/1996 | Lin | |
| 5,556,395 A | * 9/1996 | Shimmick et al. | 606/4 |
| 5,599,340 A | 2/1997 | Simon et al. | |
| 5,683,379 A | 11/1997 | Hohla | |
| 5,782,822 A | 7/1998 | Telfair et al. | |
| 5,964,748 A | * 10/1999 | Peyman | 606/5 |
| 6,004,313 A | 12/1999 | Shimmick et al. | |
| 6,056,740 A | * 5/2000 | Shimmick | 606/5 |
| 6,090,100 A | * 7/2000 | Hohla | 606/5 |
| 6,149,643 A | * 11/2000 | Herekar et al. | 606/5 |
| 6,245,059 B1 | * 6/2001 | Clapham | 606/5 |
| 6,287,299 B1 | * 9/2001 | Sasnet et al. | 606/12 |
| 6,319,247 B1 | * 11/2001 | Hofer et al. | 606/5 |
| 6,322,216 B1 | * 11/2001 | Yee et al. | 351/210 |

FOREIGN PATENT DOCUMENTS

EP 628298 12/1994

* cited by examiner

Primary Examiner—Linda C. M. Dvorak
Assistant Examiner—A. Farah
(74) Attorney, Agent, or Firm—Townsend and Townsend and Crew LLP; Mark D. Barrish, Esq.

(57) ABSTRACT

Laser eye surgery systems, methods, and devices makes use of a two-pivot scanning system for laterally deflecting the laser beam across the corneal surface to provide X-Y scanning. An imaging lens pivots about two eccentric axes extending along, but disposed beyond the laser beam. As the lens pivots, the beam will follow a substantially arc-shaped path. The eccentric axes are offset about the laser beam axis by about 90°, and the system controller can compensate for the arc-shaped path deflections by adjusting the angular position of the imaging lens about complementary stage.

24 Claims, 5 Drawing Sheets

TWO-PIVOT SCANNING FOR LASER EYE SURGERY

BACKGROUND OF THE INVENTION

1. Field of the Invention

The present invention is generally related to ophthalmic instruments and surgery. In a particular embodiment, the invention provides a mechanism and method for scanning a laser beam over a surface of a patient's eye to effect resculpting.

Laser-based systems are now used in ophthalmological surgery on the surface of the cornea to correct vision defects. These systems use lasers to achieve a desired change in corneal shape, with the laser removing thin layers of corneal tissue using a technique generally described as ablative photodecomposition. These laser eye surgery techniques are useful in procedures such as photorefractive keratectomy, phototherapeutic keratectomy, laser insitu keratomileusis (LASIK), and the like.

The ability to track or follow movements of a patient's tissue is recognized as a desirable feature in laser eye surgery systems. Movements of the eye include both voluntary movements and involuntary movements. In other words, even when the patient is holding "steady" fixation on a visual target, eye movement still occurs. Tracking of the eye during laser eye surgery has been proposed to avoid uncomfortable structures which attempt to achieve total immobilization of the eye. Tracking may enhance known laser eye surgery procedures, and may also facilitate new procedures, such as treatment of irregular astigmatism.

A variety of structures and techniques have been proposed for both tracking of eye movements and scanning of a laser beam across the corneal tissue. An exemplary "offset imaging" scanning system is described in European Patent Application Publication No. 628298, the full disclosure of which is hereby incorporated by reference. This offset imaging system allows a relatively large beam to be accurately directed onto the corneal surface so as to mitigate myopia, hyperopia, astigmatism, and combinations of these ocular defects, particularly when the scanning or offset imaging system is combined with one or more variable apertures for profiling the laser beam. As described in co-pending U.S. patent application Ser. No. 09/274,499, filed Mar. 23, 1999, and entitled Multiple Beam Laser Sculpting System and Method, the laser beam may ideally be separated into a plurality of beamlets to minimize discontinuities adjacent the ablation edges.

Although known scanning systems have proven both effective and safe for resculpting the cornea to improve vision, work in connection with the present invention has shown that integrating eye tracking capabilities into known laser eye surgery systems can present additional challenges. Specifically, laser eye surgery systems having eye tracking capabilities would benefit from enhanced response time of the beam deflection mechanism. Although alternative scanning systems having potentially faster response times have been described, the offset imaging system described above remains popular, possibly in part because of the combination of accuracy of safety provided by this known mechanism.

In light of the above, it would be desirable to provide improved laser eye surgery systems, devices, and methods. It would be particularly beneficial if these improvements provided enhanced scanning techniques which maintained the accuracy and safety of known scanning systems, and provided faster response times. It would be particularly beneficial if these improvements allowed the incorporation of eye trackers into known laser eye surgery systems, ideally without having to modify the entire optical train and control architecture.

2. The Background Art

As described above, European Patent Application Publication No. 682298 entitled "System for Laser Treatment of Refractive Errors" describes an exemplary scanning mechanism for use in laser eye surgery. Alternative scanning mechanisms and related structures and methods are described in U.S. Pat. Nos. 4,669,466; 4,665,913; 5,782,822; 5,599,340; 5,520,679; 4,887,019; 5,391,165; 5,683,379; and 5,505,723; the fall disclosures of which are incorporated herein by reference.

SUMMARY OF THE INVENTION

The present invention generally provides laser eye surgery systems, methods, and devices. The invention makes use of a two-pivot scanning system for laterally deflecting the laser beam across the corneal surface in two dimensions (sometimes called X-Y scanning). In the exemplary embodiment, an imaging lens pivots about two eccentric pivots having pivotal axes extending along, but disposed outside the laser beam. As the lens pivots along one of the two axes, the beam will follow an arc-shaped path. The eccentric axes are typically perpendicular to the laser beam and are ideally offset from each other about the laser beam axis by about 90°, so that pivoting of the imaging lens about the second eccentric axis will move the laser along an orthogonal arc-shaped path. The system controller can compensate for these arc-shaped path deflections by adjusting the angular position of the complementary axes, thereby allowing the beam to be accurately directed at a target location throughout a target X-Y region of the corneal surface.

In a first aspect, the invention provides a laser eye surgery system for modifying a cornea of a patient. The system comprises a laser generating a laser beam for selectively ablating the cornea. The laser beam defines a beam axis. A first stage is pivotable relative to the laser about a first axis offset laterally from the beam. A second stage is pivotable relative to the first stage about a second axis offset laterally from the beam. An optical element is mounted to the second stage in an optical path of the laser beam. The optical element deflects the beam laterally with pivoting of the first and second stages.

The optical element will preferably comprise an imaging lens. A controller will often be coupled to the first and second stages so that the stages pivot in response to signals from the controller. The controller may compensate for arc-shaped beam deflection paths of the beam to accurately direct the laser beam at a target location.

Preferably, the first stage will pivot relative to a fixed support structure by driving engagement of a first motor which is fixed relative to a fixed support structure. The first stage may carry a pivotal joint coupling the first stage to a second stage, so that the second eccentric axis moves with the first stage. A second drive motor may be mounted to the first stage, with the second drive motor drivingly engaging the second stage. Sensors will preferably indicate stage angular positions to the controller to ensure targeting accuracy.

In another aspect, the invention provides a laser eye surgery system for modifying a cornea of a patient. The system comprises a laser generating a laser beam for selectively ablating the cornea. The laser beam defines a beam axis. An optical train in an optical path of the laser beam directs the laser beam toward the cornea. A first offset mechanism pivots at least a portion of the optical train about a first eccentric axis. A second offset mechanism pivots at least a portion of the optical train about a second eccentric axis. The first eccentric axis and the second eccentric axis extend along the beam axis and are offset relative to each other circumferentially about the beam, often by 90°.

In another aspect, the invention provides a scanning system for use with a laser eye surgery system. The laser system has a laser producing a laser beam for selectively resculpting a cornea according to signals from a controller. The scanning system comprises a first stage which pivots relative to the laser about a first axis in response to the control signals. The first axis is offset laterally from the beam axis. A second stage is pivotably mounted to the first stage. The second stage pivots about a second axis offset laterally from the beam axis in response to the control signals. An optical element is mounted to the second stage in an optical path of the laser beam to deflect the beam laterally according to the control signals so as to effect the desired resculpting.

In a method aspect, the invention allows redirecting of a corneal resculpting laser beam. The method comprises deflecting a beam along a substantially arc-shaped path by rotating an optical element about a first pivot or axis offset laterally from the beam. The beam is deflected along a substantially arc-shaped path by rotating the optical element about a second pivot or axis offset laterally from the beam, and offset circumferentially about the beam from the first axis. Typically, the pivots are offset by about 90° relative to the beam. The two intercepting arc-shaped beam deflection paths which this method can provide allow substantially rectangular coverage of a patient's cornea.

DESCRIPTION OF THE SPECIFIC EMBODIMENTS

Figure 1:
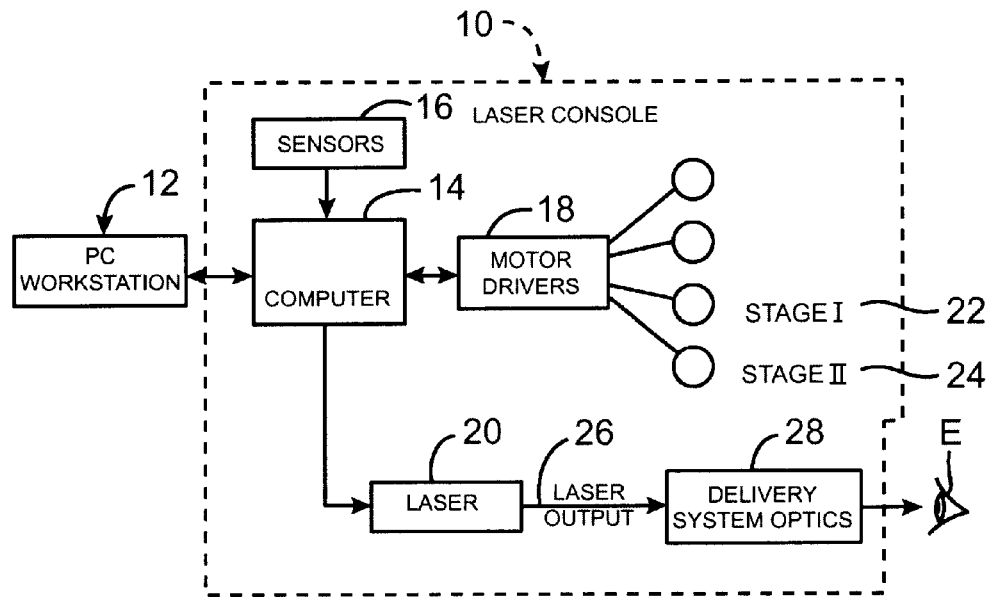
FIG. 1 is a simplified block diagram of an ophthalmological surgery system incorporating the invention.

Referring now to FIG. 1, an ophthalmological surgery system 10 generally includes a laser 20 which generates a laser beam 26 that is selectively directed toward eye E by delivery system optics 28. Delivery system optics 28 scan beam 26 over the corneal tissue of eye E according to instructions from computer 14. The computer generally scans beam 26 over eye E by changing the angular position of first and second stage pivot systems 22, 24 (described below). Optionally, computer 14 may further profile beam 26 using one or more variable apertures.

As shown in FIG. 1, system 10 includes a personal computer workstation 12 coupled to a computer 14. Laser surgery system 10 includes a plurality of sensors (generally designated by reference number 16) which produce feedback signals from moveable mechanical and optical components, some of which will be described hereinbelow. Optionally, sensors 16 may further include a system for tracking movement of the eye. PC workstation 12 and computer 14 may also be combined in a signal processor structure, or the processing functions performed by these structures may be distributed in a wide variety of alternative arrangements.

In response to signals provided from the sensors, and according to the resculpting to be performed on the eye to alleviate an optical defect, computer 14 transmits command signals to motor drivers 18 and to laser 20. In response to these command signals, the motor drivers produce signals to change an angular orientation of first stage pivot system 22, to change an angular position of a second stage pivot system 24, and to operate the other components of the laser delivery system, such as a variable diameter iris, to control the distance between a pair of cylinder blades, to rotate an angular orientation of the cylinder blades, and the like.

Figure 2:
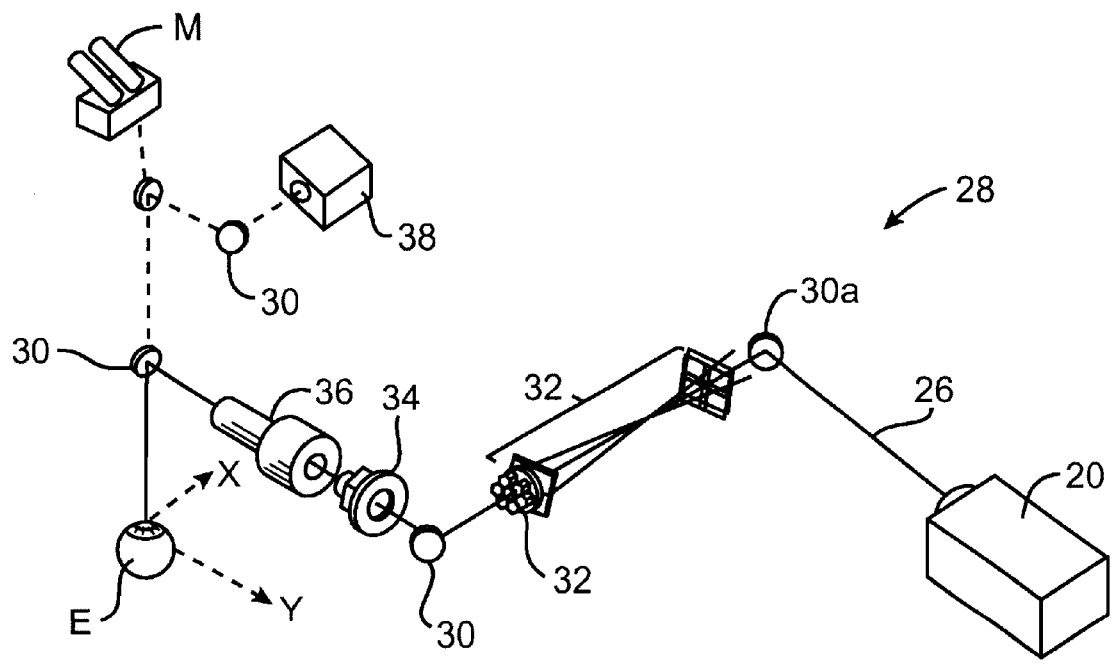
FIG. 2 is a schematic diagram of the delivery system optics.

Typical delivery system optics 28 are illustrated without their associated support structure in FIG. 2. Mirrors 30 direct laser beam 26 through spatial and temporal integrators 32 and a variable aperture 34 prior to entering a scanning mechanism 36. Scanning mechanism 36 (which includes the first and second stages) selectively deflects beam 26 laterally across the corneal surface of eye E in the X-Y plane. A variety of lenses may be provided for imaging, viewing the procedure using microscope M, and the like. Optionally, a tracking system 38 monitors movement of eye E, so that computer 14 can compensate for the eye movement and accurately ablate the intended portion of the treatment area. A wide variety of tracking systems might be used to sense these lateral movements of the eye, and these tracking arrangements are generally well described in the patent literature. A particularly advantageous eye tracker is commercially available from ISCAN, INC. of Burlington, Mass. Ideally, tracking system 38 and scanning mechanism 36 are suitable for integration into STAR™ and STAR S2™ laser eye surgery systems, which are commercially available from VISX, Incorporated of Sunnyvale, Calif.

Laser 20 may include, but is not limited to, an excimer laser such as an argon-fluoride excimer laser producing laser energy with a wavelength of about 193 nm. Alternative laser systems may include solid state lasers, such as frequency multiplied solid state lasers, flash-lamp and diode pumped solid state lasers, and the like. Exemplary solid state lasers include UV solid state lasers producing wavelengths of approximately 188–240 nm such as those disclosed in U.S. Pat Nos. 5,144,630,and 5,742,626,and in Borsuztky et al., "Tunable UV Radiation at Short Wavelengths (188–240 um) Generated by Frequency Mixing in Lithium Borate", Appl. Phys. 61:529–532 (1995). A variety of alternative lasers might also be used. The laser energy will generally comprise a beam formed as a series of discreet laser pulses, and the pulses may be separated into a plurality of beamlets.

Figure 3:
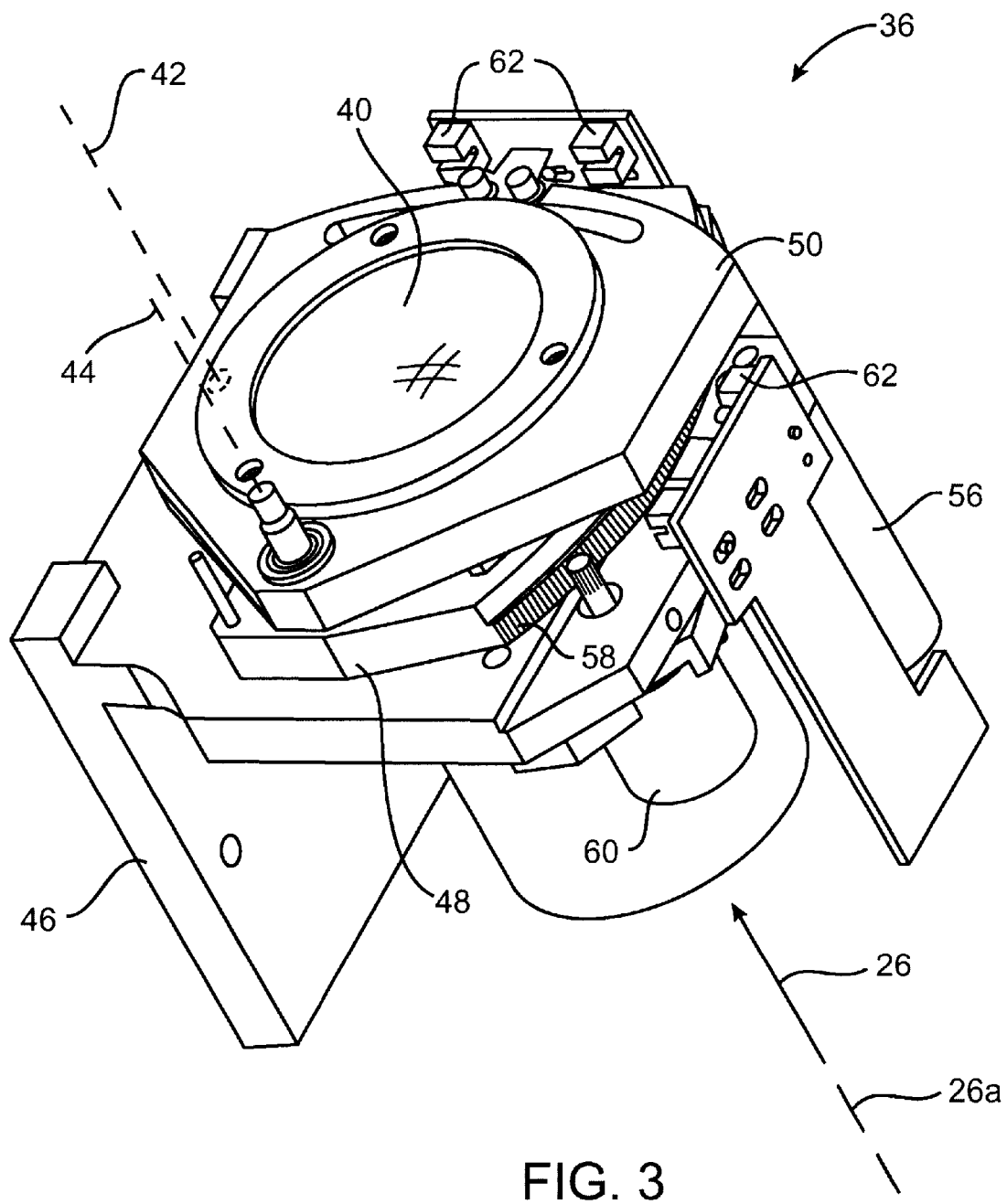
FIG. 3 is a perspective view of a scanning mechanism having first and second stages which pivot an offset imaging lens about first and second eccentric axes.
Figure 3A:
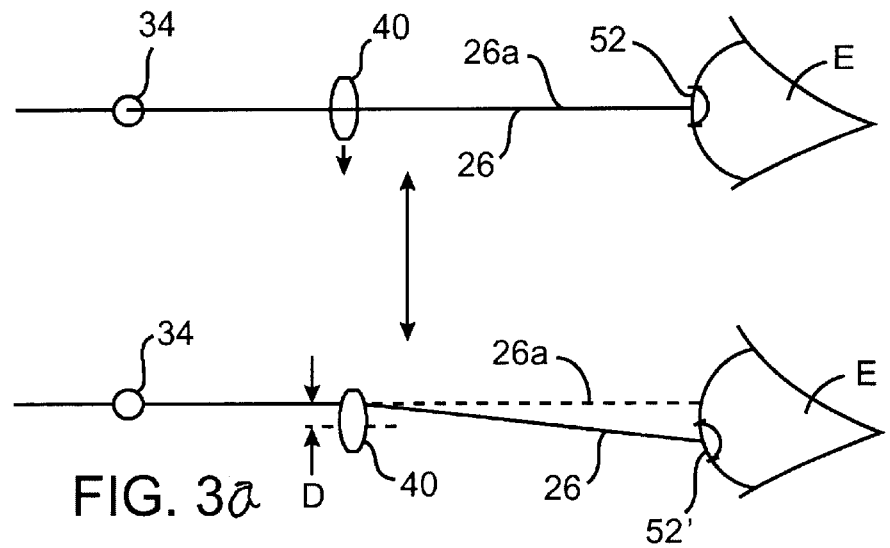
FIG. 3A schematically illustrates laterally displacing an image of an aperture on either side of an initial axis by variably offsetting an imaging lens to either side of the undeflected laser beam.

The scanning mechanism is seen most clearly in FIG. 3. The scanning mechanism 36 generally laterally deflects laser beam 26 by pivoting an imaging lens 40 about a first axis 42, and about a second axis 44. More specifically, scanning mechanism 36 includes a fixed support structure in the form of bracket 46. A first stage 48 pivots about first axis 42 relative to bracket 46, while a second stage 50 pivots relative to first stage 48 about second axis 44.

The deflection of beam 26 from an undeflected beam axis 26a can be understood with reference to 3 and 3A. By pivoting the first and second stages about pivotal axes extending along and outside of beam 26, imaging lens 40 is displaced by a variable distance D from initial beam axis 26a. Displacing imaging lens 40 from initial axis 26a displaces an image 52 of variable aperture 34 from initial axis 26a to an offset aperture image 52'. The amount and direction of movement of the aperture image is related (but not necessarily proportional) to the amount and direction of lens offset D. Hence, to reposition aperture image 52 across the corneal surface, the offset structure moving lens 40 will preferably allow the lens to be moved directly both above and below initial axis 26 as illustrated in FIG. 3, and also into and out of the plain of the drawing, thereby allowing scanning of the ablative laser energy in the X-Y plane across the corneal tissue.

Figure 4:
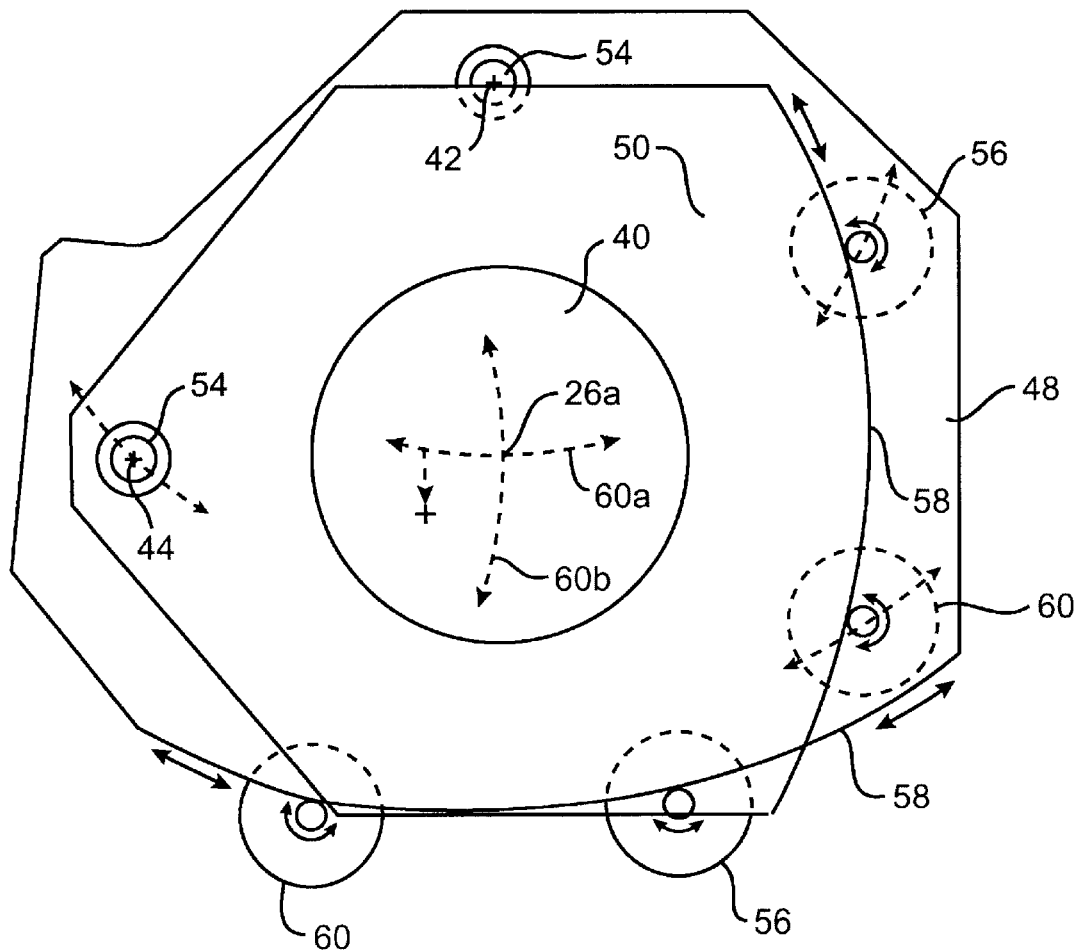
FIG. 4 is an axial view showing how the angular orientations of the first and second axes move an axis of a laser beam along substantially arc-shaped paths, and how a controller can compensate for movement along these paths to accurately scan the laser beam in the X-Y plane.

The X-Y scanning capabilities of scanning mechanism 36 can further be understood with reference to FIGS. 3 and 4. First stage 48 is pivotally mounted to bracket 46 by a pivotal joint 54. Pivotal joint 54 defines first pivotal axis or pivot 42, and the first stage rotates about the first pivot due to driving engagement between a motor 56 and a drive surface 58 of the first stage. An encoder 60 also engages drive surface 58, so as to provide feedback to the computer 14 regarding the angular orientation of the first stage. Second stage 50 is mounted to first stage 48 by another pivotal joint 54 defining second pivotal axis or pivot 44. Imaging lens 40 is mounted to second stage 50, so that the imaging lens moves with the first stage when the first stage pivots about pivot 42 along are 60a.

To angularly reposition the imaging lens about the second axis, a motor 56 is mounted to first stage 48 and drivingly engages a drive surface 58 of second stage 50. Feedback to computer 14 is again provided by an encoder 60, which is also mounted to first stage 48.

The pivotal motion of first stage 48 relative to bracket 46 allows imaging lens 40 to be displaced about pivot 42 along a first arc-shaped path 60a on either side of initial beam access 26a. To provide X-Y scanning of laser beam 26 to an arbitrary location within a treatment zone on a corneal surface of the eye, motor 56 mounted to first stage 48 pivots second stage 50 about pivot 44, thereby moving offset lens 40 along a second arc-shaped path 60b which intersects the first arc-shaped path. In the exemplary embodiment, pivots 42 and 44 are offset about the initial beam axis 26a by about 90°, so that the first and second arc-shaped paths 60a, 60b also intersect by about 90°.

It should be noted that the path followed by the image of the aperture need not exactly define a circular arc. Pivoting a single imaging lens about one of two pivotal joints will generally cause the deflected beam to follow a described herein as substantially arc-shaped. Alternatively, pivoting one of two cylindrical lenses (one cylindrical lens being mounted to each stage) may cause the aperture image to follow a substantially linear path.

Accurate positioning of the aperture image on the X-Y plane adjacent the corneal surface should accommodate the arc-shaped motion of the image by adjusting the angular position of the lens about the first and second pivots 42, 44.

In other words, unlike conventional cross slides (which provide linear motion, but which tend to be relatively heavy and require a relatively large amount of force to move) the present invention uses dual pivots to approximate motions in the X and Y directions, and compensates for the resulting nonlinearity of the beam deflection by additional movement of the complementary stage, as can be understood with reference to FIG. 4.

A wide variety of algorithms might be used to compensate for the arc-shaped beam deflection of the dual pivot imaging lens support of the present invention. Computer 14 may simply model the substantially arc-like movement of the laser beam based on the kinematic structure of scanning mechanism 36 and the optical properties of lens 40. Alternatively, a look up table may be created of the desired angular positions of the first and second stages for discreet X and Y target coordinates, with standard interpolation routines used between the discreet table entries.

Figure 5:
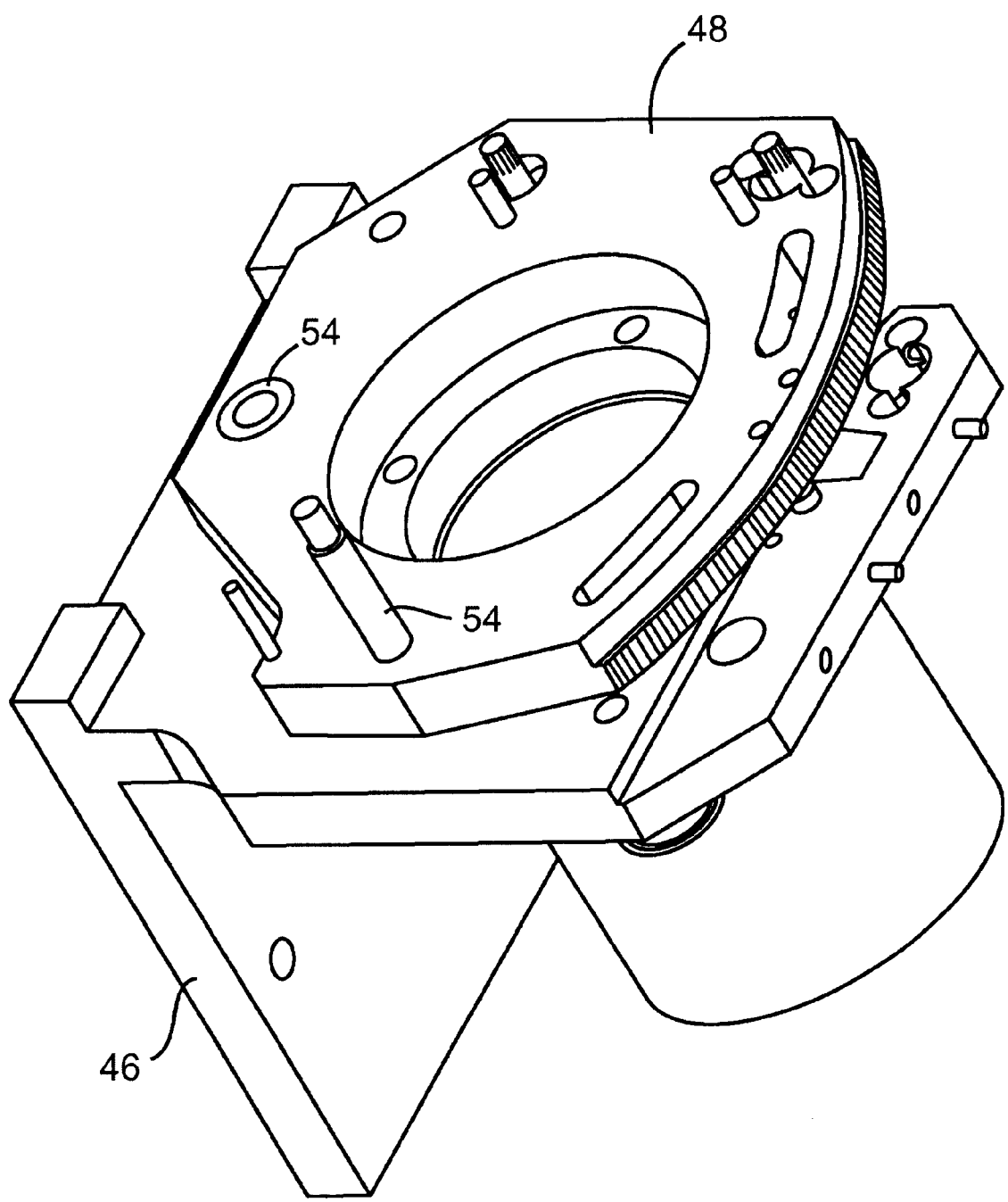
FIG. 5 is a perspective view of the scanning mechanism of FIG. 4, in which the second stage has been removed to more clearly show the first stage pivot and the second stage drive mechanism.
Figure 6:
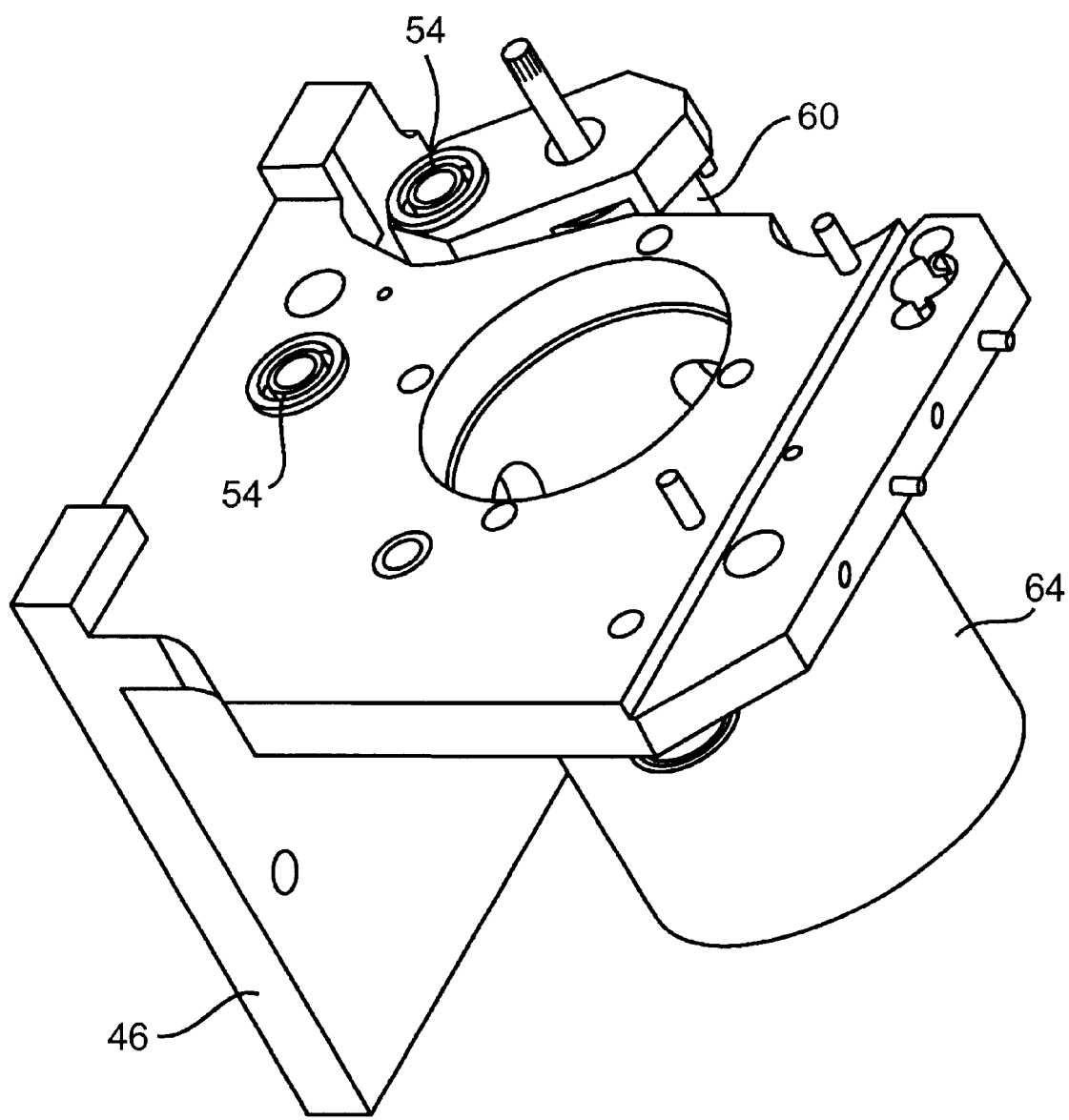
FIG. 6 is a perspective view of the fixed support structure of the scanning mechanism of FIG. 3, in which the first and second stages have been removed.

Still further details of the exemplary scanning mechanism 36 can be understood with reference to FIGS. 3, 5, and 6. Advantageously, imaging lens 40 is generally disposed between the pivot 54 supporting a stage and its associated motor 60. As a result, the lens moves only a fraction of the translation distance of drive surface 58. This improves the resolution and accuracy of the positioning of the lens. For example, as lens 40 is located roughly halfway between each pivotal joint and its associated drive motor, a driven motion of one millimeter will produce a half millimeter of lens displacement. Encoders 60 can therefore accurately measure the position of the lens 40 with a tolerance of roughly half the positional tolerance of drive surface 58. In the exemplary embodiment, motors 56 are electric motors with gear reduction drives sold commercially by MICROMO of St. Petersburg, Fla. under model No. 1624T0121S+16/7 3.7:1 K 912+X0520. The encoders are commercially available from Nemicon Corporation under Model No. OME-500-2MCA. It should be understood that a wide variety of alternative actuators and position sensors might be used, including integrated actuation and position sensing systems, stepper motors, potentiometers, and the like.

Motors 56 and optical encoders 60 engage drive surfaces 58 of the associate stage using a gear tooth drive system. The gear teeth may be directly formed in the material of the stages, with the exemplary stages being formed of a high-strength, low-friction polymer such Derlin™ polymers or the like. Limit switches 62 may be attached to the first and second stages 48, 50 to avoid damage, with the limit switches optionally being electromechanical, electro-optical, or the like. In the exemplary embodiment, motor 56 drivingly engaging first stage 48 is rigidly affixed to bracket 46, while the associated encoder 60 is pivotally mounted relative to the bracket with a biasing spring urging the gear teeth of the encoder against the gear teeth of drive surface 58. Similarly, as can be seen in FIG. 6, the encoder 60 which senses the position of second stage 50 relative to first stage 48 is pivotally mounted to the first stage by yet another pivotal joint 54, with a biasing spring urging the gear teeth of the encoder into engagement with the gear teeth of drive surface 58 of the second stage 50. The drive motor is again rigidly supported, this time to first stage 48, with its gear teeth engaging drive surface 58 as illustrated in FIG. 4.

A variety of refinements, adaptations, and modifications are possible within the scope of the present invention. For example, a tubular structure 64 may include a radially inwardly protruding circumferential rib to block light which might otherwise strike the non-optical surfaces of the first or second stage and damage scanning mechanism 36, and/or might create aberrations in the resulting ablation profile in a patient's eye. In some embodiments, separate imaging lenses may be mounted on first and second stages which pivot independently. Hence, the scope of the present invention is not limited to the specifics of the exemplary embodiment, but is instead limited solely by the appended claims.

What is claimed is:

1. A laser eye surgery system for modifying a cornea of a patient, the system comprising:
   a laser generating a laser beam for selectively ablating the cornea, the laser beam defining a beam axis;
   an optical train in an optical path of the laser beam for directing the laser beam toward the cornea;
   a first offset mechanism pivoting at least a portion of the optical train about a first eccentric axis; and
   a second offset mechanism moving at least a portion of the optical train about a second eccentric axis, the first eccentric axis and the second eccentric axis extending along the beam axis and offset circumferentially relative to the beam axis about the beam.

2. The laser eye surgery system of claim 1, wherein the first offset mechanism comprises a first stage and the second offset mechanism comprises a second stage mounted on the first stage.

3. The laser eye surgery system of claim 2, wherein a moving pivotal joint attaches the first stage to the second stage, the moving pivotal joint pivoting about the first eccentric axis when the first stage moves and defining the second eccentric axis so that the second eccentric axis moves with the first stage.

4. The laser eye surgery system of claim 2, wherein a lens is mounted to the second stage.

5. The laser eye surgery system of claim 1, further comprising a controller coupled to the first and second offset mechanisms, the controller selectively directing the beam across the cornea so as to achieve a desired resculpting.

6. The laser eye surgery of claim 5, wherein the controller calculates angular orientations of the first and second pivoting system in response to desired beam offsets relative to an optical axis of the cornea.

7. The laser eye surgery system of claim 5, wherein the first offset mechanism effects substantially arc-shaped movement of the beam.

8. The laser eye surgery system of claim 7, wherein the offset mechanism effects substantially arc-shaped movement of the beam which intersects the arc-shaped movement of the first offset mechanism so as to allow lateral movement of the beam along a plane perpendicular to an optical axis of the cornea.

9. The laser eye surgery system of claim 5, wherein the first offset mechanism moves a lens of the optical train about the first eccentric axis.

10. The laser eye surgery system of claim 9, wherein the second offset mechanism moves the lens about the second eccentric axis.

11. The laser eye surgery system of claim 5, wherein the controller varies the angular orientations of the first and second offset mechanisms in response to sensed lateral movements of the cornea.

12. The laser eye surgery system of claim 11, wherein the controller models the movement of the lens along the arcs to calculate the angular orientations of the offset mechanism.

13. A laser eye surgery system for modifying a cornea of a patient, the system comprising:
    an optical element;
    a laser generating a laser beam for selectively ablating the cornea, the laser beam defining a beam axis;
    a first stage pivotable relative to the laser beam about a first axis offset laterally from the optical element;
    a second stage pivotable relative to the first stage about a second axis offset laterally from the optical element;
    the optical element mounted to the second stage in an optical path of the laser beam, the optical element deflecting the beam laterally with pivoting of the first and second stages.

14. The system of claim 1, wherein the optical element comprises a lens.

15. The system of claim 2 wherein a controller varies the angular orientations of the first and second offset mechanisms in response to sensed lateral movements of the cornea.

16. The system of claim 1 wherein the first and second eccentric axes are offset by about 90 degrees about the beam axis.

17. A laser eye surgery system for modifying a cornea of a patient, the system comprising:
    an optical element;
    a laser generating a laser beam for selectively ablating the cornea, the laser beam defining a beam axis;
    a first stage pivotable relative to the laser beam about a first axis offset laterally from the optical element;
    a second stage pivotable relative to the first stage about a second axis offset laterally from the optical element;
    the optical element mounted to the second stage in an optical path of the laser beam, the optical element deflecting the beam laterally with pivoting of the first and second stages;
    wherein the optical element comprises a lens; and
    wherein the lens deflects the beam laterally along a first arc when the first stage moves and along a second arc when the second stage moves, the second axis being circumferentially offset about the beam axis from the first eccentric axis so that the first and second arcs intersect and the beam can be deflected along a plane perpendicular to the beam axis.

18. The system of claim 17, further comprising a controller coupled to the first and second stages so that the stages pivot in response to signals from the controller, the controller compensating for deflection of the beam along the arcs to move the beam to a desired position along the plane.

19. A laser generating a laser beam for selectively ablating the cornea, the laser beam defining a beam axis;
    a first stage pivotable relative to the laser beam about a first axis offset laterally from the beam;
    a second stage pivotable relative to the first stage about a second axis offset laterally from the beam;
    an optical element mounted to the second stage in an optical path of the laser beam, the optical element deflecting the beam laterally with pivoting of the first and second stages; and
    a first pivotal joint supporting the first stage and defining the first eccentric axis, a first motor drivingly engaging the first stage, and a first position sensor providing a signal indicating a pivotal position of the first stage, the optical element disposed between the first pivotal joint and the sensor.

20. The system of claim 19, further comprising a second pivotal joint supporting the second stage and defining the second eccentric axis, a second motor drivingly engaging the first stage, and a second position sensor providing a signal indicating a pivotal position of the second stage, the optical element disposed between the first pivotal joint and the sensor.

21. A laser eye surgery system for modifying a cornea of a patient, the system comprising:
- a laser generating a laser beam for selectively ablating the cornea, the laser beam defining a beam axis;
- a first stage pivotable relative to the laser about a first axis offset laterally from the beam;
- a second stage pivotable relative to the first stage about a second axis offset laterally from the beam;
- an optical element mounted to the second stage in an optical path of the laser beam, the optical element deflecting the beam laterally with pivoting of the first and second stages;
- a first pivotal joint offset laterally from the optical element, the first pivotal joint supporting the first stage and defining the first eccentric axis, a first motor drivingly engaging the first stage, and a first position sensor providing a signal indicating a pivotal position of the first stage, the optical element disposed between the first pivotal joint and the sensor;
- a second pivotal joint offset laterally from the optical element, the first pivotal joint supporting the second stage and defining the second eccentric axis, a second motor drivingly engaging the first stage, and a second position sensor providing a signal indicating a pivotal position of the second stage, the optical element disposed between the first pivotal joint and the sensor; and
- wherein the second pivotal joint, the second motor, and the second position sensor are mounted to the first stage to pivot with the first stage about the first pivotal joint.

22. A laser eye surgery system for modifying a cornea of a patient, the system comprising:
- a laser generating a laser beam for selectively ablating the cornea, the laser beam defining a beam axis;
- an optical train in an optical path of the laser beam for directing the laser beam toward the cornea;
- a first offset mechanism pivoting at least a portion of the optical train about a first eccentric axis;
- a second offset mechanism moving at least a portion of the optical train about a second eccentric axis, the first eccentric axis and the second eccentric axis extending along the beam axis and offset circumferentially relative to the beam axis about the beam; and
- a controller coupled to the first and second offset mechanisms, the controller selectively directing the beam across the cornea so as to achieve a desired resculpting;
- wherein the first offset mechanism moves a lens of the optical train about the first eccentric axis;
- wherein the second offset mechanism moves the lens about the second eccentric axis; and
- wherein the first and second eccentric axes are offset by about 90 degrees about the beam axis.

23. A laser eye surgery system for modifying a cornea of a patient, the system comprising:
- a laser generating a laser beam for selectively ablating the cornea, the laser beam defining a beam axis;
- an optical train in an optical path of the laser beam for directing the laser beam toward the cornea;
- a first offset mechanism pivoting at least a portion of the optical train about a first eccentric axis; and
- a second offset mechanism moving at least a portion of the optical train about a second eccentric axis, the first eccentric axis and the second eccentric axis extending along the beam axis and offset circumferentially relative to the beam axis about the beam;
- wherein the first offset mechanism comprises a first cylindrical lens mounted on a first pivotable stage and the second offset mechanism comprises a second cylindrical lens mounted on a second pivotable stage.

24. A method for redirecting a corneal resculpting laser beam having a beam axis, the method comprising:
- deflecting the beam along a first substantially arc-shaped path by rotating an optical element about a first axis, the first axis extending along and offset laterally from the beam;
- deflecting the beam along a second substantially arc-shaped path by rotating the optical element about a second axis, the second axis extending along the beam and offset laterally from the beam, the second axis also offset circumferentially about the beam axis from the first axis.

* * * * *